(12) United States Patent
Auger et al.

(10) Patent No.: US 8,546,424 B2
(45) Date of Patent: Oct. 1, 2013

(54) ACETYLENE DERIVATIVES OF 5-PHENYL-PYRAZOLOPYRIDINE, PREPARATION THEREOF, AND THERAPEUTIC USE THEREOF

(75) Inventors: Florian Auger, Paris (FR); Luc Even, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/395,819

(22) PCT Filed: Sep. 17, 2010

(86) PCT No.: PCT/FR2010/051931
§ 371 (c)(1),
(2), (4) Date: Jul. 11, 2012

(87) PCT Pub. No.: WO2011/033229
PCT Pub. Date: Mar. 24, 2011

(65) Prior Publication Data
US 2012/0270897 A1    Oct. 25, 2012

(30) Foreign Application Priority Data
Sep. 18, 2009   (FR) ..................... 09 56445

(51) Int. Cl.
A61K 31/437   (2006.01)
A61P 25/08    (2006.01)
A61P 25/00    (2006.01)
A61P 29/00    (2006.01)
A61P 25/30    (2006.01)
A61P 35/00    (2006.01)
A61P 25/24    (2006.01)
C07D 471/04   (2006.01)

(52) U.S. Cl.
USPC .......................................... 514/300; 546/121

(58) Field of Classification Search
USPC .......................................... 514/300; 546/121
See application file for complete search history.

(56) References Cited

FOREIGN PATENT DOCUMENTS
EP    1389618 A1    2/2004
WO    WO01/83479 A2    11/2001
WO    WO2004/026871 A1    4/2004

OTHER PUBLICATIONS

Schweizer, Edward E. et al., "Reactions of Azines. 9. Preparation of 4,5-Dihydropyrazolo[1,5-a]pyridines, 6,7-Dihydropyrazolo[1,5-a]pyridines, and Pyrazolo[1,5-a]pyridines," Journal of Organic Chemistry (1987), vol. 52, pp. 1319-1324.
International Search Report dated Feb. 17, 2011 issued in PCT/FR2010/051931.
U.S. Office Action dated Mar. 20, 2013 issued in U.S. Appl. No. 13/496,118.

*Primary Examiner* — Niloofar Rahmani
(74) *Attorney, Agent, or Firm* — Scully, Scott, Murphy & Presser, P.C.

(57) ABSTRACT

Compounds of formula (I):

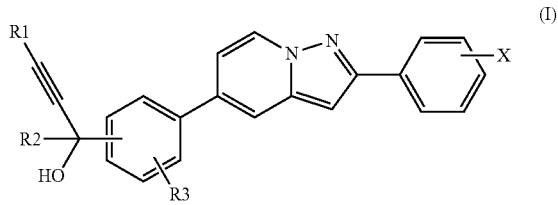

in which:
R1 and R2 represent, independently of one another, a hydrogen atom or a ($C_1$-$C_6$)alkyl group,
R3 represents one or more hydrogen or halogen atoms,
X represents from 1 to 4 substituents, identical to or different from one another, chosen from hydrogen, halogen or ($C_1$-$C_6$)alkyl,
in the form of the base or of an addition salt with an acid.
Therapeutic use and synthetic process.

6 Claims, No Drawings

ACETYLENE DERIVATIVES OF 5-PHENYL-PYRAZOLOPYRIDINE, PREPARATION THEREOF, AND THERAPEUTIC USE THEREOF

The present invention relates to acetylenic 5-phenylpyrazolopyridine derivatives, to their preparation and to their therapeutic application in the treatment or prevention of diseases involving Nurr-1 nuclear receptors, also known as NR4A2, NOT, TINUR, RNR-1 and HZF3.

A subject-matter of the present invention is the compounds of formula (I):

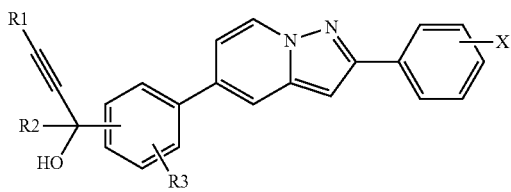

in which:
R1 and R2 represent, independently of one another, a hydrogen atom or a $(C_1$-$C_6)$alkyl group,
R3 represents one or more hydrogen or halogen atoms,
X represents from 1 to 4 substituents, identical to or different from one another, chosen from hydrogen, halogen or $(C_1$-$C_6)$alkyl,
in the form of the base or of an addition salt with an acid.

The compounds of formula (I) can comprise one or more asymmetric carbon atoms. They can thus exist in the form of enantiomers or diastereoisomers. These enantiomers and diastereoisomers, and their mixtures, including the racemic mixtures, come within the invention.

The compounds of formula (I) can exist in the form of bases or of addition salts with acids. Such addition salts come within the invention.

These salts can be prepared with pharmaceutically acceptable acids but the salts of other acids, for example of use in the purification or the isolation of the compounds of formula (I), also come within the invention.

The compounds of formula (I) can also exist in the form of hydrates or solvates, namely in the form of combinations or associations with one or more molecules of water or with a solvent. Such hydrates and solvates also come within the invention.

In the context of the present invention:
a $(C_x$-$C_t)$ group is understood to mean a group comprising between x and t carbon atoms;
a halogen atom is understood to mean a fluorine, a chlorine, a bromine or an iodine;
an alkyl group is understood to mean a saturated, linear, branched or cyclic, aliphatic group optionally substituted by a saturated, linear, branched or cyclic, alkyl group. Mention may be made, by way of examples, of the methyl, ethyl, propyl, isopropyl, butyl, isobutyl, tert-butyl, cyclopropyl, cyclobutyl, cyclopentyl, cyclohexyl, methylcyclopropyl or cyclopropylmethyl groups, and the like.

Among the compounds of formula (I) which are subject-matters of the invention, a first group of compounds is composed of the compounds in which:

X represents a halogen atom or a $(C_1$-$C_6)$alkyl group;

R1 and R2 represent a hydrogen atom or a $(C_1$-$C_6)$alkyl group;

R3 represents one or more hydrogen or halogen atoms, in the form of the base or of an addition salt with an acid.

Among the compounds of formula (I) which are subject-matters of the invention, a second group of compounds is composed of the compounds in which:

X represents a chlorine, a fluorine or a methyl group;

R1 and R2 represent a hydrogen atom or a methyl group;

R3 represents a hydrogen atom or a difluoro group, in the form of the base or of an addition salt with an acid.

Mention may in particular be made, among the compounds of formula (I) which are subject-matters of the invention, of the following compounds:

1-{3-[2-(4-Chlorophenyl)pyrazolo[1,5-a]pyridin-5-yl]phenyl}prop-2-yn-1-ol

1-{3-[2-(4-Fluorophenyl)pyrazolo[1,5-a]pyridin-5-yl]phenyl}prop-2-yn-1-ol

1-{3-[2-(4-Fluorophenyl)pyrazolo[1,5-a]pyridin-5-yl]phenyl}but-2-yn-1-ol

2-{3-[2-(4-Fluorophenyl)pyrazolo[1,5-a]pyridin-5-yl]phenyl}but-3-yn-2-ol

1-{2-[2-(4-Fluorophenyl)pyrazolo[1,5-a]pyridin-5-yl]phenyl}prop-2-yn-1-ol

1-{2,6-Difluoro-3-[2-(4-fluorophenyl)pyrazolo[1,5-a]pyridin-5-yl]phenyl}prop-2-yn-1-ol 1-{3-[2-(2-Fluorophenyl)pyrazolo[1,5-a]pyridin-5-yl]phenyl}prop-2-yn-1-ol 1-[3-(2-{p-Tolyl}pyrazolo[1,5-a]pyridin-5-yl)phenyl]prop-2-yn-1-ol (−)-1-{3-[2-(4-Fluorophenyl)pyrazolo[1,5-a]pyridin-5-yl]phenyl}prop-2-yn-1-ol (+)-1-{3-[2-(4-Fluorophenyl)pyrazolo[1,5-a]pyridin-5-yl]phenyl}prop-2-yn-1-ol (−)-2-{3-[2-(4-Fluorophenyl)pyrazolo[1,5-a]pyridin-5-yl]phenyl}but-3-yn-2-ol (+)-2-{3-[2-(4-Fluorophenyl)pyrazolo[1,5-a]pyridin-5-yl]phenyl}but-3-yn-2-ol In accordance with the invention, the compounds of general formula (I) can be prepared according to the process described in Scheme 1.

Scheme 1

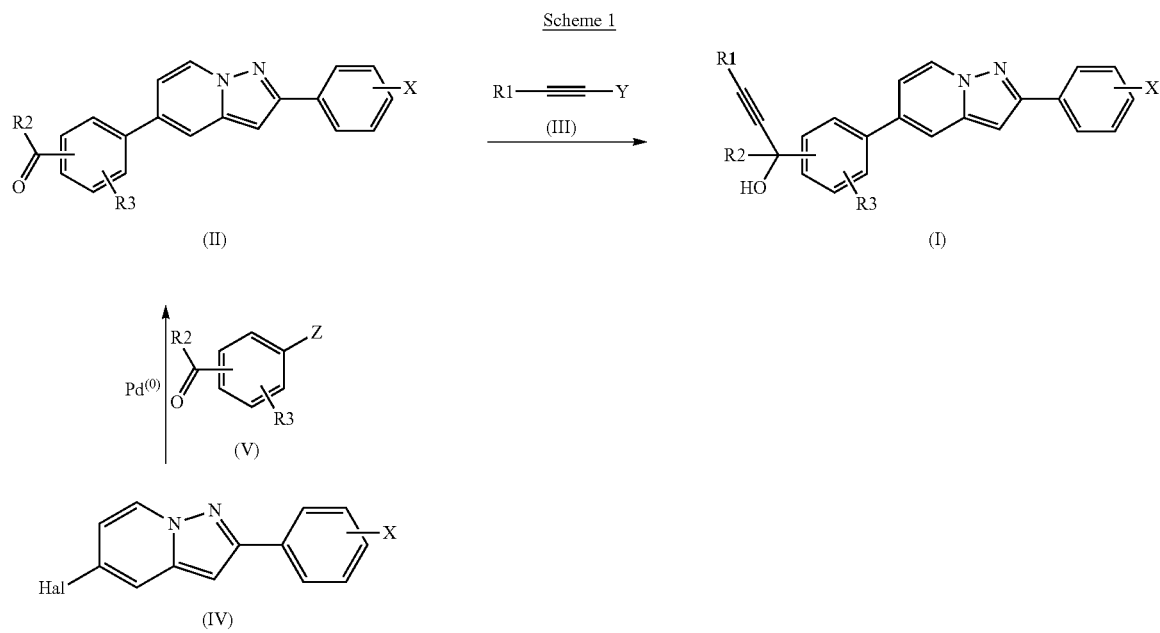

The compounds of the invention can be prepared according to Scheme 1 by the action of an organometallic derivative of general formula (III), in which R1 is defined as above and Y represents a metal derivative, for example a magnesium halide, on a carbonyl derivative of general formula (II), in which R2, R3 and X are defined as above, in order to obtain the compounds of general formula (I), for example according to the method described by S. Chassaing, M. Kueny-Stotz, G. Isorez and R. Brouillard in *Eur. J. Org. Chem.*, 2007, 2438.

The compounds of general formula (II), in which R2, R3 and X are defined as above, can be obtained by a coupling reaction catalysed by metal, such as palladium, between a pyrazolopyridine of general formula (IV), in which X is defined as above and Hal represents a halogen atom, and a carbonyl derivative of general formula (V), in which R2 and R3 are defined as above and Z represents a boron or tin derivative, for example according to the method described by A. Gueiffier in *Helv. Chim. Acta*, 2001, 84, 3610.

In accordance with the invention, the compounds of general formula (IV) can be prepared according to the process described in Scheme 2.

Scheme 2

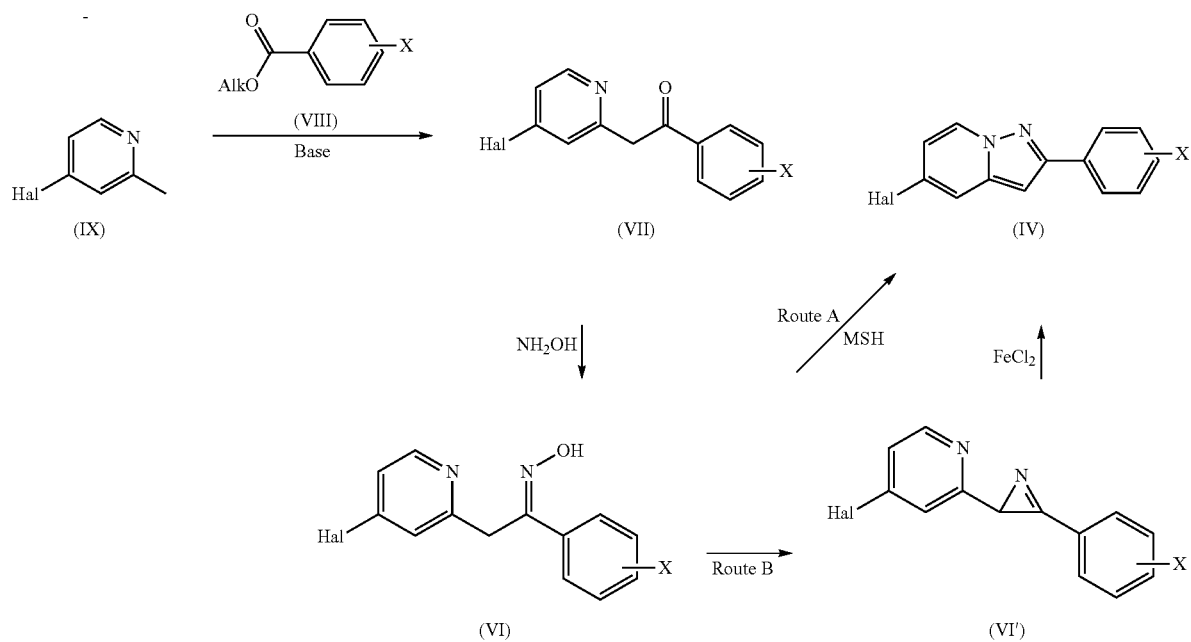

In Scheme 2, Route A, the compounds of general formula (IV), in which X is defined as above and Hal represents a halogen atom, can be prepared by the action of O-(mesitylenesulphonyl)hydroxylamine (MSH) on a compound of general formula (VI), in which X and Hal are defined as above, for example according to the method described by Y. Tamura, J.-H. Kim, Y. Miki, H. Hayashi and M. Ikeda, in *J. Het. Chem.*, 1975, 12, 481.

In Scheme 2, Route B, the compounds of general formula (IV), in which X is defined as above and Hal represents a halogen atom, can also be prepared by conversion of the compounds of general formula (VI) into compounds of general formula (VI'), in which X and Hal are defined above, by the action of an acid anhydride, such as trifluoroacetic anhydride, in the presence of a base, such as triethylamine, followed by cyclization to give compounds of general formula (IV) in the presence of a catalyst, such as ferrous chloride, for example according to the method described by K. S. Gudmundsson in *Bioorg. Med. Chem.*, 2005, 13, 5346.

The compounds (VI) can be obtained by the action of hydroxylamine on the compounds (VII).

The compounds (VII) can be obtained from the compounds (IX) by the action of the esters of general formula (VIII), in which X is defined as above and Alk represents an alkyl group, in the presence of a strong base, for example according to the method described by K. S. Gudmundsson in *Bioorg. Med. Chem.*, 2005, 13, 5346.

In Schemes 1 and 2, the starting compounds and the reactants, when their method of preparation is not described, are commercially available or are described in the literature or else can be prepared according to methods which are described therein or which are known to a person skilled in the art.

The enantiomers of the compounds of formula (I) can be obtained by resolution of the racemates, for example by chromatography on a chiral column of the Chiralpak AD 20 μm type, by elution with solvents of hydrocarbon type (for example heptane) and alcohol type (for example methanol and ethanol).

The following examples describe the preparation of certain compounds in accordance with the invention. These examples are not limiting and serve only to illustrate the present invention. The numbers of the compounds of the examples refer to those given in the table below, in which the chemical structures and physical properties of a few compounds according to the invention are illustrated.

EXAMPLE 1

1-{3-[2-(4-Chlorophenyl)pyrazolo[1,5-a]pyridin-5-yl]phenyl}prop-2-yn-1-ol (Compound 1 of the Table)

1.1 2-(4-Bromopyridin-2-yl)-1-(4-chlorophenyl) ethanone 5 g (29.07 mmol) of 4-bromo-2-methylpyridine and 11.27 g (61.04 mmol) of ethyl 4-chlorobenzoate are placed under a stream of nitrogen in a round-bottomed flask and dissolved in 50 ml of anhydrous tetrahydrofuran. The solution is cooled to 5° C. and 70 ml (70 mmol) of a lithium hexamethyldisilazane solution (1M in tetrahydrofuran) are added dropwise. After addition, the mixture is stirred at ambient temperature for 2 h and cooled to 5° C., and then 100 ml of water are gradually added. The medium is subsequently diluted with 250 ml of ethyl acetate and 100 ml of water. The organic phase is separated and the aqueous phase is extracted twice with 100 ml of ethyl acetate. The organic phases are subsequently combined, dried over sodium sulphate and filtered. 15 g of silica are subsequently added to the filtrate and the mixture is concentrated under reduced pressure. The powder obtained is used as solid deposit for chromatography on silica gel, with a mixture of cyclohexane and ethyl acetate (9/1) as eluent. 8.4 g (93%) of compound are obtained in the form of a yellow powder.

LC-MS: M+H=310
$^1$H NMR (d$_6$-DMSO) δ (ppm): 4.6 (s, 2H); 6.4 (s, 1H); 7.4 (s, 1H); from 7.5 to 7.6 (m, 6H); 7.7 (s, 1H); 7.9 (d, 2H); 8.1 (d, 2H); 8.3 (d, 1H); 8.4 (d, 1H); 15.0 (s, 1H). (Keto/enol mixture: 40/60).

1.2 2-(4-Bromopyridin-2-yl)-1-(4-chlorophenyl) ethanone oxime 8.4 g (27.05 mmol) of 2-(4-bromopyridin-2-yl)-1-(4-chlorophenyl)ethanone are placed in 150 ml of ethanol in a round-bottomed flask. 22 ml (272.56 mmol) of pyridine and 7.5 g (107.93 mmol) of hydroxylamine monohydrochloride are added. The mixture is subsequently stirred at ambient temperature for 5 hours and then the reaction medium is concentrated under reduced pressure until a pasty yellow solid is obtained, which solid is taken up in 400 ml of ethyl acetate and 400 ml of water. The organic phase is separated and the aqueous phase is extracted three times with 200 ml of ethyl acetate. The organic phases are subsequently combined, dried over sodium sulphate and filtered. The filtrate is concentrated under reduced pressure: 8.1 g (91.9%) of compound are obtained in the form of a blue powder.

LC-MS: M+H=325
$^1$H NMR (d$_6$-DMSO) δ (ppm): 4.3 (s, 2H); 7.45 (m, 2H); 7.50 (d, 1H); 7.55 (s, 1H); 7.75 (m, 2H); 8.35 (d, 1H); 11.65 (s, 1H).

1.3. 5-Bromo-2-(4-chlorophenyl)pyrazolo[1,5-a]pyridine 12.9 g (45.21 mmol) of ethyl O-(2-mesitylenesulphonyl) acetohydroxamate are placed in 30 ml of 1,4-dioxane in a round-bottomed flask. The mixture is cooled to 0° C. and 13.5 ml (156.60 mmol) of perchloric acid (70% in water) are added. 10 ml of 1,4-dioxane are subsequently added and then the medium is vigorously stirred at 0° C. for 2 h 30 minutes. The medium is subsequently poured into 350 ml of ice-cold water. The medium is left at approximately 0° C. for 10 minutes and then the white solid formed is recovered by filtration on a sintered glass funnel (do not completely dry, the product is potentially explosive in the dry state). The pasty white solid obtained is washed with 350 ml of ice-cold water and is then taken up in 250 ml of 1,2-dichloroethane and 150 ml of brine cooled to approximately 5° C. The organic phase is recovered and is filtered through a hydrophobic cartridge. The filtrate is recovered and is added dropwise to a solution, cooled to approximately 0° C., of 8.1 g (24.88 mmol) of 2-(4-bromopyridin-2-yl)-1-(4-chlorophenyl)ethanone oxime (compound obtained in stage 1.2) in 150 ml of 1,2-dichloroethane.

After the addition, the mixture is allowed to return to ambient temperature and is stirred at ambient temperature for 3 hours. 250 ml of dichloromethane, 200 ml of water and 100 ml of an aqueous NaOH solution (1N) are subsequently added successively to the medium. The mixture is left stirring and is then separated by settling. The organic phase is separated and the aqueous phase is extracted with 2 times 200 ml of dichloromethane. The organic phases are subsequently combined, filtered through a hydrophobic cartridge (70 ml liquid/liquid extraction column, Radleys®) and then mixed with 15 g of silica. The filtrate is subsequently concentrated under reduced pressure: a brown powder is obtained, which powder is used as solid deposit for chromatography on silica gel, elution being carried out with a mixture of cyclohexane and dichloromethane (1/1). 5.8 g (75%) of compound are obtained in the form of a slightly yellow fluffy solid.

LC-MS: M+H=307

$^1$H NMR (d$_6$-DMSO) δ (ppm): 7.0 (d, 1H); 7.1 (s, 1H); 7.6 (d, 2H); 8.0 (s, 1H); 8.1 (d, 2H); 8.7 (d, 1H).

1.4 3-[2-(4-Chlorophenyl)pyrazolo[1,5-a]pyridin-5-yl]benzaldehyde 0.300 g (0.98 mmol) of 5-bromo-2-(4-chlororophenyl)pyrazolo[1,5-a]pyridine, obtained according to the protocol described in 1.3, 0.292 g (1.95 mmol) of 3-formylphenylboronic acid and 0.94 g (2.88 mmol) of caesium carbonate are introduced into 5 ml of a 9/1 mixture of tetrahydrofuran and water under a stream of nitrogen. 0.08 g (0.10 mmol) of [1,1'-bis(diphenylphosphino)ferrocene]dichloropalladium (II) is added and the medium is heated at 70° C. for 2 hours. The medium is subsequently brought back to ambient temperature and then diluted with dichloromethane and water. The medium is filtered through a hydrophobic cartridge (70 ml liquid/liquid extraction column, Radleys®) and the organic phase is recovered, to which 2 g of silica are added. After evaporating the solvent, the residue is purified by chromatography on silica gel, elution being carried out with a mixture of cyclohexane and ethyl acetate (9/1). 0.302 g (93%) of the expected product is obtained in the form of a yellow powder.

Melting point (° C.): 152-154

LC-MS: M+H=333

$^1$H NMR (d$_6$-DMSO) δ (ppm): 7.2 (s, 1H); 7.35 (d, 1H); 7.55 (d, 2H); 7.75 (t, 1H); 7.95 (d, 1H); 8.05 (d, 2H); 8.15 (s, 1H); 8.20 (d, 1H); 8.40 (s, 1H); 8.85 (d, 1H); 10.15 (s, 1H).

1.5 1-{3-[2-(4-Chlorophenyl)pyrazolo[1,5-a]pyridin-5-yl]phenyl}prop-2-yn-1-ol 0.100 g (0.30 mmol) of 3-[2-(4-chlorophenyl)pyrazolo[1,5-a]pyridin-5-yl]benzaldehyde, obtained according to 1.4, is dissolved in 8 ml of tetrahydrofuran under a stream of nitrogen. The medium is cooled to 0° C. for slow addition of 0.800 ml (0.40 mmol) of an ethynylmagnesium bromide solution (0.5 M in tetrahydrofuran). The medium is subsequently brought back to ambient temperature and then stirred for 45 minutes. Hydrolysis is carried out by adding, under cold conditions and dropwise, a saturated aqueous ammonium chloride solution and then dilution is carried out with 40 ml of ethyl acetate and 30 ml of water. The organic phase is recovered and the aqueous phase is extracted twice with 20 ml of ethyl acetate. The organic phases are subsequently combined and then concentrated under reduced pressure, after having added 1 g of silica. The residue is subsequently purified by chromatography on silica gel, elution of the solid deposit being carried out with a mixture of cyclohexane and ethyl acetate (9/1). 0.02 g (18%) of the expected product is obtained in the form of a beige powder.

Melting point (° C.): 195-197.

LC-MS: M+H=359

$^1$H NMR (d$_6$-DMSO) δ (ppm): 3.55 (s, 1H); 5.50 (m, 1H); 6.15 (d, 1H); 7.20 (s, 1H); 7.30 (d, 1H); 7.60 (m, 4H); 7.80 (m, 1H); 7.90 (s, 1H); 8.00 (m, 3H); 8.80 (d, 1H).

EXAMPLE 2

1-{3-[2-(4-Fluorophenyl)pyrazolo[1,5-a]pyridin-5-yl]phenyl}prop-2-yn-1-ol (Compound 2 of the Table)

2.1 2-(4-Bromopyridin-2-yl)-1-(4-fluorophenyl)ethanone 5.0 g (29.07 mmol) of 4-bromo-2-picoline and 10.2 g (60.95 mmol) of ethyl 4-fluoro-benzoate are placed under a stream of nitrogen in a round-bottomed flask and dissolved in 50 ml of anhydrous tetrahydrofuran. The solution is cooled to 0° C. and 70 ml (70 mmol) of a lithium hexamethyldisilazane solution (1M in tetrahydrofuran) are added dropwise. After addition, the mixture is stirred at ambient temperature for 2 h before being cooled to 5° C. and gradually adding 100 ml of water to the medium. The medium is subsequently diluted with 250 ml of ethyl acetate and 100 ml of water. The organic phase is separated and the aqueous phase is extracted twice with 100 ml of ethyl acetate. The organic phases are subsequently combined, dried over sodium sulphate and filtered. 15 g of silica are subsequently added to the filtrate before concentrating it under reduced pressure. The powder obtained is used as solid deposit for chromatography on silica gel with a mixture of cyclohexane and ethyl acetate (9/1) as eluent. 7.5 g (88%) of compound are obtained in the form of a yellow powder.

LC-MS: M+H=294 (keto/enol ratio: 43/57)

$^1$H NMR (d$_6$-DMSO) δ (ppm): 4.56 (s, 2H); 6.34 (s, 1H); from 7.23 to 7.40 (m, 5H); 7.53 (d, 1H); 7.56 (m, 1H); 7.70 (d, 1H); from 7.81 to 7.92 (m, 2H); from 8.04 to 8.16 (m, 2H); 8.29 (d, 1H); 8.37 (d, 1H); 15.0 (s, 1H).

2.2 2-(4-Bromopyridin-2-yl)-1-(4-fluorophenyl)ethanone oxime 7.5 g (24.26 mmol) of 2-(4-bromopyridin-2-yl)-1-(4-fluorophenyl)ethanone are placed in a round-bottomed flask containing 100 ml of absolute ethanol. 20 ml (247.78 mmol) of pyridine and 7.08 g (101.88 mmol) of hydroxylamine monohydrochloride are added before leaving the medium to stir at ambient temperature for 3 h. The ethanol is subsequently evaporated under vacuum and the residue obtained is taken up in 250 ml of water and 250 ml of ethyl acetate. The organic phase is separated and then the aqueous phase is extracted 5 times with 150 ml of ethyl acetate. The organic phases are subsequently combined, dried over sodium sulphate and concentrated under vacuum. 7.82 g of compound are obtained.

LC-MS: M+H=309

$^1$H NMR (d$_6$-DMSO) δ (ppm): 4.26 (s, 2H); 7.19 (t, 2H); 7.50 (m, 2H); 7.75 (m, 2H); 8.33 (d, 1H); 11.50 (s, 1H). ((E) oxime obtained).

2.3 5-Bromo-2-(4-fluorophenyl)pyrazolo[1,5-a]pyridine 7.82 g (25.50 mmol) of 2-(4-bromopyridin-2-yl)-1-(4-fluorophenyl)ethanone oxime are placed in a round-bottomed flask and dissolved in 400 ml of 1,2-dichloroethane. 170 ml of a solution of O-(mesitylenesulphonyl)hydroxylamine (0.27M in 1,2-dichloroethane—compound obtained according to the protocol described in 1.3) is added dropwise to the medium, cooled to approximately 0° C. After the addition, the medium is stirred at ambient temperature for 1 h 30. The medium is subsequently diluted with 200 ml of water and 200 ml of a sodium hydroxide solution (1N). The two-phase medium is stirred and then separated by settling. The organic phase is separated and then the aqueous phase is extracted 4 times with 200 ml of dichloromethane. The organic phases are subsequently combined, dried over sodium sulphate and filtered. 15 g of silica are subsequently added to the filtrate before concentrating it under reduced pressure. The powder obtained is used as solid deposit for chromatography on silica gel with a mixture of cyclohexane and dichloromethane (1/1) as eluent. 5.06 g (68%) of compound are obtained in the form of a white fluffy powder.

LC-MS: M+H=291
$^1$H NMR ($d_6$-DMSO) δ (ppm): from 7.00 to 7.10 (m, 2H); 7.45 (m, 2H); 8.05 (m, 3H); 8.70 (d, 1H).

2.4 3-[2-(4-Fluorophenyl)pyrazolo[1,5-a]pyridin-5-yl]benzaldehyde 0.200 g (0.69 mmol) of 5-bromo-2-(4-fluorophenyl)pyrazolo[1,5-a]pyridine, obtained in stage 2.3, 0.125 g (0.83 mmol) of 3-formylphenylboronic acid and 0.670 g (2.06 mmol) of caesium carbonate are introduced under a stream of nitrogen into 5 ml of a 9/1 mixture of tetrahydrofuran and water. 0.055 g (0.07 mmol) of [1,1'-bis(diphenylphosphino)ferrocene]-dichloropalladium(II) is added and the medium is heated at 70° C. for 3 hours. A further 0.063 g (0.42 mmol) of 3-formylphenylboronic acid, 0.335 g (1.03 mmol) of caesium carbonate and 0.028 g (0.03 mmol) of [1,1'-bis(diphenylphosphino)ferrocene]dichloro-palladium(II) are subsequently added while leaving to stir at 70° C. for 4 h. The medium is subsequently brought back to ambient temperature and then diluted with dichloromethane and water. The two-phase medium is filtered through a hydrophobic cartridge (70 ml liquid/liquid extraction column, Radleys®) and the organic phase is recovered, to which 1.2 g of silica are added. After evaporating the solvent, the residue is purified by chromatography on silica gel, elution being carried out with a mixture of cyclohexane and ethyl acetate (8/2). 0.175 g (80%) of the expected product is obtained in the form of a white powder.

LC-MS: M+H=317
$^1$H NMR ($d_6$-DMSO) δ (ppm): 7.15 (s, 1H); from 7.30 to 7.37 (m, 3H); 7.77 (t, 1H); 7.98 (m, 1H); 8.08 (m, 2H); 8.15 (m, 1H); 8.20 (m, 1H); 8.38 (s, 1H); 8.82 (d, 1H); 10.15 (s, 1H).

2.5 1-{3-[2-(4-Fluorophenyl)pyrazolo[1,5-a]pyridin-5-yl]phenyl}prop-2-yn-1-ol 0.100 g (0.32 mmol) of 3-[2-(4-fluorophenyl)pyrazolo[1,5-a]pyridin-5-yl]benzaldehyde, obtained in stage 2.4, is dissolved in 8 ml of tetrahydrofuran under a stream of nitrogen. The medium is cooled to 5° C. for solidation of 2 ml (1 mmol) of an ethynylmagnesium bromide solution (0.5M in tetrahydrofuran). The medium is gradually brought back to ambient temperature and then stirred for 30 minutes. Hydrolysis is carried out by adding, under cold conditions and dropwise, a saturated aqueous ammonium chloride solution and then the medium is diluted with 50 ml of dichloromethane and 40 ml of water. The medium is subsequently floated through a hydrophobic cartridge (70 ml of liquid/liquid extraction column, Radleys®) and the organic phase is recovered, to which 1 g of silica is added before concentrating under reduced pressure. The residue is purified by chromatography on silica gel, elution of the solid deposit being carried out with a mixture of cyclohexane and ethyl acetate (7/3). 0.055 g (50%) of the expected product is obtained in the form of a white powder.

Melting point (° C.): 192-194
LC-MS: M+H=343

$^1$H NMR ($d_6$-DMSO) δ (ppm): 3.55 (s, 1H); 5.50 (m, 1H); 6.15 (d, 1H); 7.10 (s, 1H); 7.20 (d, 1H); 7.35 (m, 2H); 7.55 (q, 2H); 7.75 (q, 1H); 7.90 (s, 1H); 8.00 (s, 1H); 8.10 (m, 2H); 8.80 (d, 1H).

EXAMPLE 3

1-{3-[2-(4-Fluorophenyl)pyrazolo[1,5-a]pyridin-5-yl]phenyl}but-2-yn-1-ol (Compound 3 of the Table)

The procedure described in stage 2.5 is followed, starting with 0.300 g (0.95 mmol) of 3-[2-(4-fluorophenyl)pyrazolo[1,5-a]pyridin-5-yl]benzaldehyde obtained according to the process described in 2.4, in solution in 10 ml of tetrahydrofuran, followed by addition of 5.70 ml (2.85 mmol) of a (propyn-1-yl)magnesium bromide solution (0.5M in tetrahydrofuran) and after chromatography on silica gel, elution being carried out with a mixture of cyclohexane and ethyl acetate (8/2), 0.23 g (67%) of the expected product is obtained in the form of a pale yellow powder.

Melting point (° C.): 164-166
LC-MS: M+H=357
$^1$H NMR ($d_6$-DMSO) δ (ppm): 1.87 (s, 3H); 5.45 (m, 1H); 5.95 (d, 1H); 7.12 (s, 1H); 7.25 (dd, 1H); 7.32 (t, 2H); 7.53 (m, 2H); 7.75 (m, 1H); 7.86 (s, 1H); 7.99 (m, 1H); 8.08 (m, 2H); 8.78 (d, 1H).

EXAMPLE 4

2-{3-[2-(4-Fluorophenyl)pyrazolo[1,5-a]pyridin-5-yl]phenyl}but-3-yn-2-ol (Compound 4 of the Table)

4.1 1-{3-[2-(4-Fluorophenyl)pyrazolo[1,5-a]pyridin-5-yl]phenyl}ethanone

The procedure described in stage 2.4 is followed, starting with 0.300 g (1.03 mmol) of 5-bromo-2-(4-fluorophenyl)pyrazolo[1,5-a]pyridine obtained in stage 2.3, 0.185 g (1.13 mmol) of 3-acetylphenylboronic acid, 1.00 g (3.09 mmol) of caesium carbonate and 0.084 g (0.10 mmol) of [1,1'-bis(diphenylphosphino)ferrocene]dichloropalladium(II) in 5 ml of a 9/1 mixture of tetrahydrofuran and water. After chromatography on silica gel, elution being carried out with a mixture of cyclohexane and ethyl acetate (8/2), 0.268 g (78%) of the expected product is obtained in the form of a beige powder.

$^1$H NMR ($d_6$-DMSO) δ (ppm): 2.70 (s, 3H); 7.10 (s, 1H); 7.32 (m, 3H); 7.68 (m, 1H); from 7.95 to 8.12 (m, 5H); 8.32 (m, 1H); 8.80 (d, 1H).

4.2 2-{3-[2-(4-Fluorophenyl)pyrazolo[1,5-a]pyridin-5-yl]phenyl}but-3-yn-2-ol The procedure described in stage 2.5 is followed, starting with 0.261 g (0.79 mmol) of 1-{3-[2-(4-fluorophenyl)pyrazolo[1,5-a]pyridin-5-yl]phenyl}ethanone obtained in stage 4.1, in solution in 10 ml of tetrahydrofuran, followed by addition of 4.74 ml (2.37 mmol) of an ethynylmagnesium bromide solution (0.5M in tetrahydrofuran) and after chromatography on silica gel, elution being carried out with a mixture of cyclohexane and dichloromethane (1/9), 0.018 g (6%) of the expected product is obtained in the fowl of a white powder.

Melting point (° C.): 215-217
LC-MS: M+H=357

¹H NMR (d₆-DMSO) δ (ppm): 1.75 (s, 3H); 3.58 (s, 1H); 6.20 (s, 1H); 7.12 (s, 1H); 7.25 (m, 1H); 7.32 (t, 2H); 7.53 (m, 1H); 7.65 (m, 1H); 7.75 (m, 1H); 7.98 (m, 2H); 8.08 (m, 2H); 8.80 (d, 1H).

EXAMPLE 5

1-{2-[2-(4-Fluorophenyl)pyrazolo[1,5-a]pyridin-5-yl]phenyl}prop-2-yn-1-ol (Compound 5 of the Table)

5.1 2-[2-(4-Fluorophenyl)pyrazolo[1,5-a]pyridin-5-yl]benzaldehyde

The procedure described in stage 2.4 is followed, starting with 0.300 g (1.03 mmol) of 5-bromo-2-(4-fluorophenyl)pyrazolo[1,5-a]pyridine obtained in stage 2.3, 0.170 g (1.13 mmol) of 2-formylphenylboronic acid, 1.00 g (3.09 mmol) of caesium carbonate and 0.084 g (0.10 mmol) of [1,1'-bis(diphenylphosphino)ferrocene]dichloropalladium(II) in 5 ml of a 9/1 mixture of tetrahydrofuran and water. After chromatography on silica gel, elution being carried out with a mixture of cyclohexane and ethyl acetate (85/15), 0.254 g (77%) of the expected product is obtained in the form of a beige powder.

LC-MS: M+H=317
¹H NMR (d₆-DMSO) δ (ppm): 7.05 (d, 1H); 7.12 (s, 1H); 7.35 (t, 2H); 7.78 (m, 2H); 7.78 (s, 1H); 7.81 (m, 1H); 8.00 (d, 1H); 8.05 (m, 2H); 8.80 (d, 1H); 10.05 (s, 1H).

5.2 1-{2-[2-(4-Fluorophenyl)pyrazolo[1,5-a]pyridin-5-yl]phenyl}prop-2-yn-1-ol The procedure described in stage 2.5 is followed, starting with 0.245 g (0.77 mmol) of 2-[2-(4-fluorophenyl)pyrazolo[1,5-a]pyridin-5-yl]benzaldehyde obtained in stage 5.1, in solution in 15 ml of tetrahydrofuran, followed by addition of 4.65 ml (2.32 mmol) of an ethynylmagnesium bromide solution (0.5M in tetrahydrofuran) and after chromatography on silica gel, elution being carried out with dichloromethane, 0.08 g (30%) of the expected product is obtained in the form of a pale yellow powder.

Melting point (° C.): 104-106
LC-MS: M+H=343
¹H NMR (d₆-DMSO) δ (ppm): 3.50 (s, 1H); 5.35 (m, 1H); 6.12 (m, 1H); 6.95 (dd, 1H); 7.12 (s, 1H); from 7.30 to 7.40 (m, 3H); 7.46 (m, 1H); 7.52 (m, 1H); 7.69 (m, 1H); 7.83 (m, 1H); 8.07 (m, 2H); 8.78 (d, 1H).

EXAMPLE 6

1-{2,6-Difluoro-3-[2-(4-fluorophenyl)pyrazolo[1,5-a]pyridin-5-yl]-phenyl}prop-2-yn-1-ol (Compound 6 of the Table)

6.1 2,6-Difluoro-3-[2-(4-fluorophenyl)pyrazolo[1,5-a]pyridin-5-yl]benzaldehyde The procedure described in stage 2.4 is followed, starting with 0.300 g (1.03 mmol) of 5-bromo-2-(4-fluorophenyl)pyrazolo[1,5-a]pyridine obtained in stage 2.3, 0.210 g (1.13 mmol) of 2,4-difluoro-3-formylphenylboronic acid, 1.00 g (3.09 mmol) of caesium carbonate and 0.084 g (0.10 mmol) of [1,1'-bis(diphenylphosphino)ferrocene]-dichloropalladium(II) in 5 ml of a 9/1 mixture of tetrahydrofuran and water. After chromatography on silica gel, elution being carried out with a mixture of cyclohexane and ethyl acetate (8/2), 0.278 g (76%) of the expected product is obtained in the fowl of a beige powder.

LC-MS: M+H=353
¹H NMR (d₆-DMSO) δ (ppm): 7.12 (m, 1H); 7.20 (s, 1H); from 7.30 to 7.50 (m, 3H); 7.95 (m, 1H); from 8.05 to 8.15 (m, 3H); 8.85 (d, 1H), 10.32 (s, 1H).

6.2 1-{2,6-Difluoro-3-[2-(4-fluorophenyl)pyrazolo[1,5-a]pyridin-5-yl]phenyl}prop-2-yn-1-ol The procedure described in stage 2.5 is followed, starting with 0.270 g (0.77 mmol) of 2,6-difluoro-3-[2-(4-fluorophenyl)pyrazolo[1,5-a]pyridin-5-yl]benzaldehyde obtained in stage 6.1, in solution in 15 ml of tetrahydrofuran, followed by addition of 4.60 ml (2.30 mmol) of an ethynylmagnesium bromide solution (0.5M in tetrahydrofuran) and after chromatography on silica gel, elution being carried out with a mixture of cyclohexane and dichloromethane (1/3), 0.171 g (57%) of the expected product is obtained in the form of a pale yellow powder.

Melting point (° C.): 151-153
LC-MS: M+H=379
¹H NMR (d₆-DMSO) δ (ppm): 3.50 (s, 1H); 5.75 (s, 1H); 6.28 (d, 1H); 7.05 (m, 1H); 7.15 (s, 1H); from 7.25 to 7.38 (m, 3H); 7.70 (m, 1H); 7.85 (s, 1H); 8.05 (m, 2H); 8.78 (d, 1H).

EXAMPLE 7

1-{3-[2-(2-Fluorophenyl)pyrazolo[1,5-a]pyridin-5-yl]phenyl}prop-2-yn-1-ol (Compound 7 of the Table)

7.1 5-Bromo-2-(2-fluorophenyl)pyrazolo[1,5-a]pyridine 1 g (5.81 mmol) of 4-bromo-2-methylpyridine and 1.88 g (12.20 mmol) of methyl 2-fluorobenzoate are placed in a round-bottomed flask and dissolved in 25 ml of anhydrous tetrahydrofuran under a stream of nitrogen. The solution is cooled to 5° C. and 14 ml (14 mmol) of a lithium hexamethyldisilazane solution (1M in tetrahydrofuran) are added dropwise. After addition, the mixture is stirred at ambient temperature for 2 h 30 and cooled to 5° C., and then 15 ml of water are gradually added. The medium is subsequently diluted with 100 ml of ethyl acetate and 100 ml of water. The organic phase is separated and the aqueous phase is extracted with 100 ml of ethyl acetate. The organic phases are subsequently combined, dried over sodium sulphate and filtered. 6 g of silica are subsequently added to the filtrate and the mixture is concentrated under reduced pressure. The powder obtained is used as solid deposit for chromatography on silica gel with a mixture of cyclohexane and ethyl acetate (95/5) as eluent. 1.71 g of a yellow powder are recovered, which powder is placed in a round-bottomed flask in the presence of 1.60 g (23.02 mmol) of hydroxylamine hydrochloride, 5 ml (61.95 mmol) of pyridine and 30 ml of ethanol. The medium is left stirring overnight at ambient temperature and then the reaction medium is concentrated under reduced pressure. The residue obtained is taken up in 50 ml of ethyl acetate and 50 ml of water. The organic phase is recovered and then the aqueous phase is extracted with 50 ml of ethyl acetate. The organic phases are subsequently combined, dried over sodium sulphate and then concentrated under reduced pressure. 1.05 g of an orange wax are obtained, which wax is placed in a round-bottomed flask containing 50 ml of 1,2-dichloroethane. The mixture is then cooled to approximately 5° C. and then 61 ml of a solution of O-(mesitylenesulphonyl)

hydroxylamine in 1,2-dichloroethane (c=0.11 mol/l) are added dropwise. The medium is stirred overnight at a.t. and then 50 ml of water, 50 ml of an aqueous NaOH solution (1N) and 100 ml of dichloromethane are added. The organic phase is recovered and then the aqueous phase is extracted with 100 ml of dichloromethane. The organic phases are subsequently combined, dried over sodium sulphate and filtered. 5 g of silica are subsequently added to the filtrate and then the mixture is concentrated under reduced pressure. The powder obtained is used as solid deposit for chromatography on silica gel with a mixture of cyclohexane and ethyl acetate (8/2) as eluent. 0.675 g (39.9%) of the expected product is recovered in the form of a yellow powder.

LC-MS: M+H=291

$^1$H NMR ($d_6$-DMSO) δ (ppm): 7.03 (d, 1H); 7.1 (dd, 1H); from 7.33 to 7.43 (m, 2H); from 7.48 to 7.55 (m, 1H); from 8.05 to 8.18 (m, 2H); 8.73 (d, 1H).

7.2 3-[2-(2-Fluorophenyl)pyrazolo[1,5-a]pyridin-5-yl]benzaldehyde

The procedure described in stage 2.4 is followed, starting with 0.150 g (0.52 mmol) of 5-bromo-2-(2-fluorophenyl)pyrazolo[1,5-a]pyridine obtained in stage 7.1, 0.092 g (0.61 mmol) of 3-formylphenylboronic acid, 0.502 g (1.54 mmol) of caesium carbonate and 0.042 g (0.050 mmol) of [1,1'-bis(diphenylphosphino)ferrocene]dichloropalladium(II) in 5 ml of a 9/1 mixture of tetrahydrofuran and water. After chromatography on silica gel, elution being carried out with a mixture of cyclohexane and ethyl acetate (8/2), 0.130 g (79%) of the expected product is obtained in the form of a beige powder.

LC-MS: M+H=317

$^1$H NMR ($d_6$-DMSO) δ (ppm): 7.10 (m, 1H); from 7.35 to 7.45 (m, 3H); 7.50 (m, 1H); 7.78 (t, 1H); 7.98 (m, 1H); from 8.15 to 8.25 (m, 3H); 8.38 (s, 1H); 8.88 (d, 1H); 10.15 (s, 1H).

7.3 1-{3-[2-(2-Fluorophenyl)pyrazolo[1,5-a]pyridin-5-yl]phenyl}prop-2-yn-1-ol The procedure described in stage 2.5 is followed, starting with 0.125 g (0.40 mmol) of 3-[2-(2-fluorophenyl)pyrazolo[1,5-a]pyridin-5-yl]benzaldehyde obtained in stage 7.2, in solution in 15 ml of tetrahydrofuran, followed by addition of 3.50 ml (1.75 mmol) of an ethynylmagnesium bromide solution (0.5M in tetrahydrofuran) and after chromatography on silica gel, elution being carried out with a mixture of cyclohexane and ethyl acetate (8/2), 0.112 g (82%) of the expected product is obtained in the fatm of a beige powder.

Melting point (° C.): 157-159

LC-MS: M+H=343

$^1$H NMR ($d_6$-DMSO) δ (ppm): 3.55 (d, 1H); 5.55 (m, 1H); 6.15 (m, 1H); 7.12 (m, 1H); 7.30 (m, 1H); from 7.32 to 7.45 (m, 2H); from 7.46 to 7.52 (m, 1H); 7.55 (m, 2H); 7.78 (m, 1H); 7.90 (s, 1H); 8.08 (s, 1H); 8.15 (m, 1H); 8.82 (d, 1H).

EXAMPLE 8

1-[3-(2-{p-Tolyl}pyrazolo[1,5-a]pyridin-5-yl)phenyl]prop-2-yn-1-ol (Compound 8 of the Table)

8.1 2-(4-Bromopyridin-2-yl)-1-(p-tolyl)ethanone 1 g (5.81 mmol) of 4-bromo-2-methylpyridine and 1.75 g (11.60 mmol) of methyl 4-methylbenzoate are placed in a round-bottomed flask and dissolved in 30 ml of anhydrous tetrahydrofuran under a stream of nitrogen. The solution is cooled to 5° C. and 14 ml (14 mmol) of a lithium hexamethyldisilazane solution (1M in tetrahydrofuran) are added dropwise. After addition, the mixture is stirred at ambient temperature for 2 h 30 and then cooled to 5° C., before gradually adding 20 ml of water. The medium is subsequently diluted with 200 ml of ethyl acetate and 200 ml of water. The organic phase is separated, dried over sodium sulphate and filtered. 5 g of silica are subsequently added to the filtrate before concentrating it under reduced pressure. The powder obtained is used as solid deposit for chromatography on silica gel with a mixture of cyclohexane and ethyl acetate (95/5) as eluent. 1.03 g (61%) of compound are obtained in the form of a yellow powder.

LC-MS: M+H=290

8.2 4-Bromo-2-(3-{p-tolyl}-2H-azirin-2-yl)pyridine 1.03 g of 2-(4-bromopyridin-2-yl)-1-(p-tolyl)ethanone, obtained in stage 8.1, are placed in a round-bottomed flask with 0.99 g (14.2 mmol) of hydroxylamine monohydrochloride, 3 ml (37 mmol) of pyridine and 100 ml of ethanol. The reaction medium is left stirring overnight and is then concentrated under reduced pressure. The residue obtained is then taken up in 200 ml of ethyl acetate and 200 ml of water. The organic phase is recovered, dried over sodium sulphate and then concentrated under reduced pressure. 1.10 g of compound are recovered and are dissolved in a round-bottomed flask containing 0.660 ml (4.74 mmol) of triethylamine and 30 ml of dichloromethane. The reaction medium is subsequently cooled to approximately 5° C. and then 0.200 ml (1.42 mmol) of trifluoroacetic anhydride are added dropwise. The medium was subsequently stirred at ambient temperature for 3 hours before being hydrolysed with 100 ml of water. The medium is subsequently stirred for 10 minutes before being filtered through a hydrophobic cartridge (70 ml liquid/liquid extraction column, Radleys®). 1.2 g of silica are subsequently added to the filtrate before concentrating it under reduced pressure. The powder obtained is used as solid deposit for chromatography on silica gel with a mixture of cyclohexane and ethyl acetate (95/5) as eluent. 0.746 g (77%) of the expected compound is recovered in the form of a white powder.

$^1$H NMR ($d_6$-DMSO) δ (ppm): 2.42 (d, 3H); 3.45 (s, 1H); from 7.42 to 7.58 (m, 4H); 7.78 (m, 2H); 8.30 (d, 1H).

8.3 5-Bromo-2-(p-tolyl)pyrazolo[1,5-a]pyridine 0.746 g of 4-bromo-2-(3-{p-tolyl}-2H-azirin-2-yl)pyridine, obtained in stage 8.2, are dissolved in the presence of 6.6 mg (0.052 mmol) of iron(II) chloride in 30 ml of 1,2-dimethoxyethane. The medium is then brought to reflux for 6 hours. A further 10 mg (0.078 mmol) of iron(II) chloride are subsequently added and the mixture is subsequently again left to stir at reflux for 3 hours. The medium is then diluted with 50 ml of ethyl acetate and 50 ml of water. The organic phase is subsequently recovered, dried over sodium sulphate and then filtered. 2 g of silica are subsequently added to the filtrate before concentrating it under reduced pressure. The powder obtained is used as solid deposit for chromatography on silica gel with a mixture of cyclohexane and ethyl acetate (85/15) as eluent. 0.534 g (71%) of the expected compound is recovered in the form of a yellow powder.

LC-MS: M+H=287

$^1$H NMR ($d_6$-DMSO) δ (ppm): 2.48 (m, 3H); 7.00 (m, 2H); 7.32 (m, 2H); 7.88 (m, 2H); 8.00 (m, 1H); 8.68 (d, 1H).

8.4 3-(2-{p-Tolyl}pyrazolo[1,5-a]pyridin-5-yl)benzaldehyde

The procedure described in stage 2.4 is followed, starting with 0.157 g (0.54 mmol) of 5-bromo-2-(p-tolyl)pyrazolo[1,5-a]pyridine obtained in stage 8.3, 0.098 g (0.65 mmol) of 3-formylphenylboronic acid, 0.535 g (1.64 mmol) of caesium carbonate and 0.045 g (0.055 mmol) of [1,1'-bis(diphenylphosphino)ferrocene]dichloropalladium(II) in 5 ml of a 9/1 mixture of tetrahydrofuran and water. After chromatography on silica gel, elution being carried out with a mixture of cyclohexane and ethyl acetate (8/2), 0.110 g (65%) of the expected product is obtained in the form of a beige powder.

LC-MS: M+H=313

$^1$H NMR (d$_6$-DMSO) δ (ppm): 2.38 (s, 3H); 7.12 (s, 1H); 7.32 (m, 3H); 7.78 (m, 1H); from 7.90 to 8.00 (m, 3H); 8.12 (m, 1H); 8.20 (m, 1H); 8.38 (s, 1H); 8.80 (d, 1H); 10.15 (s, 1H).

8.5 1-[3-(2-{p-Tolyl}pyrazolo[1,5-a]pyridin-5-yl)phenyl]prop-2-yn-1-ol

The procedure described in stage 2.5 is followed, starting with 0.105 g (0.34 mmol) of 3-(2-{p-tolyl}pyrazolo[1,5-a]pyridin-5-yl)benzaldehyde obtained in stage 8.4, in solution in 15 ml of tetrahydrofuran, followed by addition of 3.20 ml (1.60 mmol) of an ethynylmagnesium bromide solution (0.5M in tetrahydrofuran) and after chromatography on silica gel, elution being carried out with a mixture of cyclohexane and ethyl acetate (8/2), 0.062 g (54%) of the expected product is obtained in the form of a yellow powder.

Melting point (° C.): 183-185.

LC-MS: M+H=339

$^1$H NMR (d$_6$-DMSO) δ (ppm): 2.40 (s, 3H); 3.55 (d, 1H); 5.55 (m, 1H); 6.15 (m, 1H); 7.10 (s, 1H); 7.22 (m, 1H); 7.32 (m, 2H); 7.55 (m, 2H); 7.78 (m, 1H); from 7.90 to 7.95 (m, 3H); 7.95 (s, 1H); 8.80 (d, 1H).

EXAMPLE 9

(−)-1-{3-[2-(4-Fluorophenyl)pyrazolo[1,5-a]pyridin-5-yl]phenyl}prop-2-yn-1-ol (Compound 9 of the Table)

0.217 g of 1-{3-[2-(4-fluorophenyl)pyrazolo[1,5-a]pyridin-5-yl]phenyl}prop-2-yn-1-ol, obtained as described in Example 2, are injected on a column containing 1200 g of Chiralpak AD 20 μm chiral stationary phase (8*35 cm). Elution is carried out at 140 ml and then 180 ml per minute with a mixture of heptane, ethanol and methanol (70/15/15) as eluent. The enantiomer (−)-1-{3-[2-(4-fluorophenyl)pyrazolo[1,5-a]pyridin-5-yl]phenyl}prop-2-yn-1-ol is eluted first (retention time=60 min). After concentrating under reduced pressure, 0.106 g of the expected product is obtained in the form of a white powder.

Melting point (° C.): 147-149.

LC-MS: M+H=343

$^1$H NMR (d$_6$-DMSO) δ (ppm): 3.55 (s, 1H); 5.50 (m, 1H); 6.15 (d, 1H); 7.10 (s, 1H); 7.20 (d, 1H); 7.35 (m, 2H); 7.55 (q, 2H); 7.75 (q, 1H); 7.90 (s, 1H); 8.00 (s, 1H); 8.10 (m, 2H); 8.80 (d, 1H).

Optical rotation: α$_D$=−6.9° (c=0.427 g/dl, DMSO, 589 nm)

Enantiomeric purity: 99.5% (on a Chiralpak AD-H 5 μm column (250*4.6 mm) with a hexane/ethanol/methanol (70/15/15) mixture as eluent (1 ml/min), retention time of 18.51 min)

EXAMPLE 10

(+)-1-{3-[2-(4-Fluorophenyl)pyrazolo[1,5-a]pyridin-5-yl]phenyl}prop-2-yn-1-ol (Compound 10 of the Table)

The enantiomer (+)-1-{3-[2-(4-fluorophenyl)pyrazolo[1,5-a]pyridin-5-yl]phenyl}prop-2-yn-1-ol is eluted in second position (retention time=80 min) during the separation carried out in Example 9. After concentrating under reduced pressure, 0.098 g of the expected product is obtained in the form of a light yellow powder.

Melting point (° C.): 139-141.

LC-MS: M+H=343

$^1$H NMR (d$_6$-DMSO) δ (ppm): 3.55 (s, 1H); 5.50 (m, 1H); 6.15 (d, 1H); 7.10 (s, 1H); 7.20 (d, 1H); 7.35 (m, 2H); 7.55 (q, 2H); 7.75 (q, 1H); 7.90 (s, 1H); 8.00 (s, 1H); 8.10 (m, 2H); 8.80 (d, 1H).

Optical rotation: α$_D$=+8.8° (c=0.502 g/dl, DMSO, 589 nm)

Enantiomeric purity: 99% (on a Chiralpak AD-H 5 μm column (250*4.6 mm) with a hexane/ethanol/methanol (70/15/15) mixture as eluent (1 ml/min), retention time of 24.58 min)

EXAMPLE 11

(−)-2-{3-[2-(4-Fluorophenyl)pyrazolo[1,5-a]pyridin-5-yl]phenyl}but-3-yn-2-ol (Compound 11 of the Table)

0.167 g of 2-{3-[2-(4-fluorophenyl)pyrazolo[1,5-a]pyridin-5-yl]phenyl}but-3-yn-2-ol, obtained as described in Example 3, is injected on a column containing 1200 g of Chiralpak AD 20 μm chiral stationary phase (8*35 cm). Elution is carried out at 250 ml per minute with a mixture of heptane, ethanol and methanol (70/15/15) as eluent. The enantiomer (−)-2-{3-[2-(4-fluorophenyl)pyrazolo[1,5-a]pyridin-5-yl]phenyl}but-3-yn-2-ol is eluted first (retention time=32 min). After concentrating under reduced pressure, 0.082 g of the expected product is obtained in the form of a white powder.

Melting point (° C.): 122-124.

LC-MS: M+H=357

$^1$H NMR (D$_6$-DMSO) δ (ppm): 1.87 (s, 3H); 5.45 (m, 1H); 5.95 (d, 1H); 7.12 (s, 1H); 7.25 (dd, 1H); 7.32 (t, 2H); 7.53 (m, 2H); 7.75 (m, 1H); 7.86 (s, 1H); 7.99 (m, 1H); 8.08 (m, 2H); 8.78 (d, 1H).

Optical rotation: α$_D$=−14.2° (c=0.323 g/dl, MeOH, 589 nm)

Enantiomeric purity: 100% (on a Chiralpak AD-H 5 μm column (250*4.6 mm) with a hexane/ethanol/methanol (70/15/15) mixture as eluent (1 ml/min), retention time of 15.00 min)

EXAMPLE 12

(+)-2-{3-[2-(4-Fluorophenyl)pyrazolo[1,5-a]pyridin-5-yl]phenyl}but-3-yn-2-ol (Compound 12 of the Table)

The enantiomer (+)-2-{3-[2-(4-fluorophenyl)pyrazolo[1,5-a]pyridin-5-yl]phenyl}but-3-yn-2-ol is eluted in second position (retention time=44 min) during the separation carried out in Example 11. After concentrating under reduced pressure, 0.083 g of the expected product is obtained in the form of a white powder.

Melting point (° C.): 126-128.

LC-MS: M+H=357

$^1$H NMR (d$_6$-DMSO) δ (ppm): 1.87 (s, 3H); 5.45 (m, 1H); 5.95 (d, 1H); 7.12 (s, 1H); 7.25 (dd, 1H); 7.32 (t, 2H); 7.53 (m, 2H); 7.75 (m, 1H); 7.86 (s, 1H); 7.99 (m, 1H); 8.08 (m, 2H); 8.78 (d, 1H).

Optical rotation: α$_D$=+18° (c=0.244 g/dl, MeOH, 589 nm)

Enantiomeric purity: 99.5% (on a Chiralpak AD-H 5 μm column (250*4.6 mm) with a hexane/ethanol/methanol (70/15/15) mixture as eluent (1 ml/min), retention time of 21.10 min)

The tables which follow illustrate the chemical structures of general formula (I) (Table 1) and the physicochemical characteristics (Table 2) of a few examples of compounds according to the invention.

In these tables:

the "M.p." column gives the melting points of the products in degrees Celsius (° C.).

the "Position" column gives the position of substitution of the

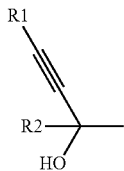

group on the phenyl nucleus (2, 3 or 4);

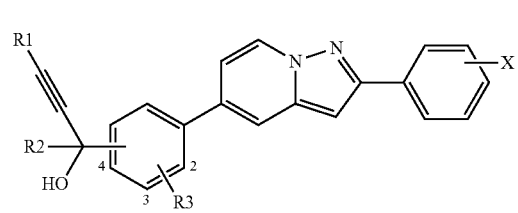

(I)

TABLE 1

| No. | R1 | R2 | R3 | Position | X | Chirality |
|---|---|---|---|---|---|---|
| 1 | H | H | H | 3 | 4-Cl | (racemic) |
| 2 | H | H | H | 3 | 4-F | (racemic) |
| 3 | Me | H | H | 3 | 4-F | (racemic) |
| 4 | H | Me | H | 3 | 4-F | (racemic) |
| 5 | H | H | H | 2 | 4-F | (racemic) |
| 6 | H | H | 2,4-diF | 3 | 4-F | (racemic) |
| 7 | H | H | H | 3 | 2-F | (racemic) |
| 8 | H | H | H | 3 | 4-Me | (racemic) |
| 9 | H | H | H | 3 | 4-F | Laevorotatory (DMSO) |
| 10 | H | H | H | 3 | 4-F | Dextrorotatory (DMSO) |
| 11 | Me | H | H | 3 | 4-F | Laevorotatory (MeOH) |
| 12 | Me | H | H | 3 | 4-F | Dextrorotatory (MeOH) |

(the solvent used to determine the optical rotation is specified in brackets)

TABLE 2

| No. | M.p. | NMR/[M + H] |
|---|---|---|
| 1 | 195-197 | $^1$H NMR (d$_6$-DMSO) δ (ppm): 3.55 (s, 1H); 5.50 (m, 1H); 6.15 (d, 1H); 7.20 (s, 1H); 7.30 (d, 1H); 7.60 (m, 4H); 7.80 (m, 1H); 7.90 (s, 1H); 8.00 (m, 3H); 8.80 (d, 1H). M + H = 359 |
| 2 | 192-194 | $^1$H NMR (d$_6$-DMSO) δ (ppm): 3.55 (s, 1H); 5.50 (m, 1H); 6.15 (d, 1H); 7.10 (s, 1H); 7.20 (d, 1H); 7.35 (m, 2H); 7.55 (q, 2H); 7.75 (q, 1H); 7.90 (s, 1H); 8.00 (s, 1H); 8.10 (m, 2H); 8.80 (d, 1H). M + H = 343 |
| 3 | 164-166 | $^1$H NMR (d$_6$-DMSO) δ (ppm): 1.87 (s, 3H); 5.45 (m, 1H); 5.95 (d, 1H); 7.12 (s, 1H); 7.25 (dd, 1H); 7.32 (t, 2H); 7.53 (m, 2H); 7.75 (m, 1H); 7.86 (s, 1H); 7.99 (m, 1H); 8.08 (m, 2H); 8.78 (d, 1H). M + H = 357 |
| 4 | 215-217 | $^1$H NMR (d$_6$-DMSO) δ (ppm): 1.75 (s, 3H); 3.58 (s, 1H); 6.20 (s, 1H); 7.12 (s, 1H); 7.25 (m, 1H); 7.32 (t, 2H); 7.53 (m, 1H); 7.65 (m, 1H); 7.75 (m, 1H); 7.98 (m, 2H); 8.08 (m, 2H); 8.80 (d, 1H). M + H = 357 |
| 5 | 104-106 | $^1$H NMR (d$_6$-DMSO) δ (ppm): 3.50 (s, 1H); 5.35 (m, 1H); 6.12 (m, 1H); 6.95 (dd, 1H); 7.12 (s, 1H); from 7.30 to 7.40 (m, 3H); 7.46 (m, 1H); 7.52 (m, 1H); 7.69 (m, 1H); 7.83 (m, 1H); 8.07 (m, 2H); 8.78 (d, 1H). M + H = 343 |
| 6 | 151-153 | $^1$H NMR (d$_6$-DMSO) δ (ppm): 3.50 (s, 1H); 5.75 (s, 1H); 6.28 (d, 1H); 7.05 (m, 1H); 7.15 (s, 1H); from 7.25 to 7.38 (m, 3H); 7.70 (m, 1H); 7.85 (s, 1H); 8.05 (m, 2H); 8.78 (d, 1H). M + H = 379 |
| 7 | 157-159 | $^1$H NMR (d$_6$-DMSO) δ (ppm): 3.55 (d, 1H); 5.55 (m, 1H); 6.15 (m, 1H); 7.12 (m, 1H); 7.30 (m, 1H); from 7.32 to 7.45 (m, 2H); from 7.46 to 7.52 (m, 1H); 7.55 (m, 2H); 7.78 (m, 1H); 7.90 (s, 1H); 8.08 (s, 1H); 8.15 (m, 1H); 8.82 (d, 1H). M + H = 343 |
| 8 | 183-185 | $^1$H NMR (d$_6$-DMSO) δ (ppm): 2.40 (s, 3H); 3.55 (d, 1H); 5.55 (m, 1H); 6.15 (m, 1H); 7.10 (m, 1H); 7.22 (m, 1H); 7.32 (m, 2H); 7.55 (m, 2H); 7.78 (m, 1H); from 7.90 to 7.95 (m, 3H); 7.95 (s, 1H); 8.80 (d, 1H). M + H = 339 |
| 9 | 147-149 | $^1$H NMR (d$_6$-DMSO) δ (ppm): 3.55 (s, 1H); 5.50 (m, 1H); 6.15 (d, 1H); 7.10 (s, 1H); 7.20 (d, 1H); 7.35 (m, 2H); 7.55 (q, 2H); 7.75 (q, 1H); 7.90 (s, 1H); 8.00 (s, 1H); 8.10 (m, 2H); 8.80 (d, 1H). M + H = 343 |
| 10 | 139-141 | $^1$H NMR (d$_6$-DMSO) δ (ppm): 3.55 (s, 1H); 5.50 (m, 1H); 6.15 (d, 1H); 7.10 (s, 1H); 7.20 (d, 1H); 7.35 (m, 2H); 7.55 (q, 2H); 7.75 (q, 1H); 7.90 (s, 1H); 8.00 (s, 1H); 8.10 (m, 2H); 8.80 (d, 1H). M + H = 343 |
| 11 | 122-124 | $^1$H NMR (d$_6$-DMSO) δ (ppm): 1.87 (s, 3H); 5.45 (m, 1H); 5.95 (d, 1H); 7.12 (s, 1H); 7.25 (dd, 1H); 7.32 (t, 2H); 7.53 (m, 2H); 7.75 (m, 1H); 7.86 (s, 1H); 7.99 (m, 1H); 8.08 (m, 2H); 8.78 (d, 1H). M + H = 357 |
| 12 | 126-128 | $^1$H NMR (d$_6$-DMSO) δ (ppm): 1.87 (s, 3H); 5.45 (m, 1H); 5.95 (d, 1H); 7.12 (s, 1H); 7.25 (dd, 1H); 7.32 (t, 2H); 7.53 (m, 2H); 7.75 (m, 1H); 7.86 (s, 1H); 7.99 (m, 1H); 8.08 (m, 2H); 8.78 (d, 1H). M + H = 357 |

The compounds according to the invention have formed the subject of pharmacological assays which make it possible to determine their modulatory effect on NOT.

Evaluation of the in vitro Activity on N2A Cells

The activity of the compounds according to the invention was evaluated on a cell line (N2A) endogenously expressing the mouse Nurr1 receptor and stably transfected with the NOT binding response element (NBRE) coupled to the luciferase reporter gene. The assays were carried out according to the procedure described below.

The Neuro-2A cell line comes from a standard commercial source (ATCC). The Neuro-2A clone was obtained, from a spontaneous tumour originating from an A albino mouse strain, by R. J Klebe et al. This Neuro-2A line is subsequently stably transfected with 8NBRE-luciferase. The N2A-8NBRE cells are cultured until confluence in 75 cm$^2$ culture flasks containing DMEM supplemented with 10% of foetal calf serum, 4.5 g/l of glucose and 0.4 mg/ml of geneticin. After a week of culture, the cells are recovered with 0.25% trypsin for 30 seconds and then resuspended in DMEM without phenol red, containing 4.5 g/l of glucose and 10% of Hyclone delipidized serum, and deposited into transparent-bottom 96-well white plates. The cells are deposited at a rate of 60 000 per well in 75 μl for 24 hours before the addition of the products. The products are applied in 25 μl and incubated for a further 24 hours. On the day of the measurement, an equivalent volume (100 μl) of Steadylite is added to each well and then left for a period of 30 minutes in order to obtain complete cell lysis and maximum signal production. The plates are subsequently measured in a luminescence counter for microplates after having been sealed with an adhesive film. The products are prepared in the form of a stock solution at $10^{-2}$M and then diluted in 100% of DMSO. Each product concentration is prediluted in culture medium before incubation with the cells, thus containing 0.625% final concentration of DMSO.

The best compounds have an $EC_{50}$ of between 0.1 nM and 10 μM.

For example, compound No. 2 showed an $EC_{50}$ value of 3 nM.

It is thus apparent that the compounds according to the invention have a modulatory effect on NOT.

The compounds according to the invention can thus be used in the preparation of medicaments for their therapeutic application in the treatment or prevention of diseases involving NOT receptors.

Thus, according to another of its aspects, a subject-matter of the invention is medicaments, which comprise a compound of formula (I) or an addition salt of the latter with a pharmaceutically acceptable acid.

These medicaments are employed therapeutically, in particular in the treatment and prevention of neurodegenerative diseases, such as, for example, Parkinson's disease, Alzheimer's disease or tauopathies (for example, progressive supranuclear palsy, frontotemporal dementia, corticobasal degeneration or Pick's disease); cerebral traumas, such as ischaemia and cranial traumas and epilepsy; psychiatric diseases, such as schizophrenia, depression, substance dependence or attention deficit hyperactivity disorders; inflammatory diseases of the central nervous system, such as multiple sclerosis, encephalitis, myelitis and encephalomyelitis, and other inflammatory diseases, such as vascular pathologies, atherosclerosis, inflammations of the joints, arthrosis or rheumatoid arthritis; osteoarthritis, Crohn's disease, ulcerative colitis; allergic inflammatory diseases, such as asthma; autoimmune diseases, such as type 1 diabetes, lupus, scleroderma, guillain-Barre syndrome, Addison's disease and other immune-mediated diseases; osteoporosis; or cancers.

These compounds might also be used as treatment associated with stem cell transplants and/or grafts.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt of the said compound, and also at least one pharmaceutically acceptable excipient.

The said excipients are chosen, depending on the pharmaceutical fat it and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its salt, can be administered in unit administration form, as a mixture with conventional pharmaceutical excipients, to animals and human beings for the prophylaxis or treatment of the above disorders or diseases.

The appropriate unit administration forms comprise oral forms, such as tablets, soft or hard gelatin capsules, powders, granules and oral solutions or suspensions, forms for sublingual, buccal, intratracheal, intraocular or intranasal administration or for administration by inhalation, forms for topical, transdermal, subcutaneous, intramuscular or intravenous administration, forms for rectal administration and implants. For topical application, the compounds according to the invention can be used in creams, gels, ointments or lotions.

By way of example, a unit administration form of a compound according to the invention in the tablet fowl can comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

There may be specific cases where higher or lower dosages are appropriate; such dosages do not depart from the scope of the invention. According to the usual practice, the dosage appropriate to each patient is determined by the physician according to the method of administration and the weight and the response of the said patient.

The present invention, according to another of its aspects, also relates to a method for the treatment of the pathologies indicated above which comprises the administration, to a patient, of an effective dose of a compound according to the invention or one of its pharmaceutically acceptable salts.

The invention claimed is:
1. A compound of formula (I):

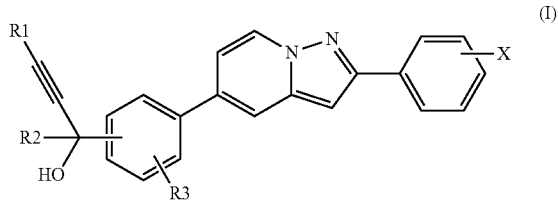

in which:
R1 and R2 represent, independently of one another, a hydrogen atom or a $(C_1-C_6)$alkyl group,
R3 represents one or more hydrogen or halogen atoms,
X represents from 1 to 4 substituents, identical to or different from one another, chosen from hydrogen, halogen or $(C_1-C_6)$ alkyl, or
in the form of the base or of an addition salt with an acid.
2. The compound according to claim 1, wherein
X represents a halogen atom or a $(C_1-C_6)$alkyl group;
R1 and R2 represent a hydrogen atom or a $(C_1-C_6)$alkyl group;
R3 represents one or more hydrogen or halogen atoms, or
in the form of the base or of an addition salt with an acid.
3. The compound according to claim 1, wherein
X represents a chlorine, a fluorine or a methyl group;
R1 and R2 represent a hydrogen atom or a methyl group;
R3 represents a hydrogen atom or a difluoro group, or
in the form of the base or of an addition salt with an acid.

4. The compound according to claim 1, corresponding to the following formulae:
- 1-{3-[2-(4-Chlorophenyl)pyrazolo[1,5-a]pyridin-5-yl]phenyl}prop-2-yn-1-ol
- 1-{3-[2-(4-Fluorophenyl)pyrazolo[1,5-a]pyridin-5-yl]phenyl}prop-2-yn-1-ol
- 1-{3-[2-(4-Fluorophenyl)pyrazolo[1,5-a]pyridin-5-yl]phenyl}but-2-yn-1-ol
- 2-{3-[2-(4-Fluorophenyl)pyrazolo[1,5-a]pyridin-5-yl]phenyl}but-3-yn-2-ol
- 1-{2-[2-(4-Fluorophenyl)pyrazolo[1,5-a]pyridin-5-yl]phenyl}prop-2-yn-1-ol
- 1-{2,6-Difluoro-3-[2-(4-fluorophenyl)pyrazolo[1,5-a]pyridin-5-yl]phenyl}prop-2-yn-1-ol
- 1-{3-[2-(2-Fluorophenyl)pyrazolo[1,5-a]pyridin-5-yl]phenyl}prop-2-yn-1-ol
- 1-[3-(2-{p-Tolyl}pyrazolo[1,5-a]pyridin-5-yl)phenyl]prop-2-yn-1-ol
- (−)-1-{3-[2-(4-Fluorophenyl)pyrazolo[1,5-a]pyridin-5-yl]phenyl}prop-2-yn-1-ol
- (+)-1-{3-[2-(4-Fluorophenyl)pyrazolo[1,5-a]pyridin-5-yl]phenyl}prop-2-yn-1-ol
- (−)-2-{3-[2-(4-Fluorophenyl)pyrazolo[1,5-a]pyridin-5-yl]phenyl}but-3-yn-2-ol
- (+)-2-{3-[2-(4-Fluorophenyl)pyrazolo[1,5-a]pyridin-5-yl]phenyl}but-3-yn-2-ol.

5. A pharmaceutical composition comprising the compound of claim 1 or an addition salt of said compound with a pharmaceutically acceptable acid.

6. The pharmaceutical composition of claim 5 further comprising at least one pharmaceutically acceptable excipient.

\* \* \* \* \*